United States Patent [19]

White

[11] Patent Number: 4,739,077

[45] Date of Patent: Apr. 19, 1988

[54] PROCESS FOR PREPARING AN AZIRIDINE DERIVATIVE

[75] Inventor: George R. White, Harpenden, England

[73] Assignee: Smith Kline & French Laboratories Limited, Welwyn Garden City, England

[21] Appl. No.: 823,240

[22] Filed: Jan. 28, 1986

[30] Foreign Application Priority Data

Jan. 31, 1985 [GB] United Kingdom ................. 8502446

[51] Int. Cl.⁴ .......................................... C07D 203/12
[52] U.S. Cl. .................................................. 548/954
[58] Field of Search ......................................... 548/954

[56] References Cited

FOREIGN PATENT DOCUMENTS 2855836 7/1979 Fed. Rep. of Germany.
2023574B 11/1982 United Kingdom.
2111044 6/1983 United Kingdom.

OTHER PUBLICATIONS

Toso et al., *Gazz. Chim. Ital.*, 110, 345–350, (1980).

Primary Examiner—Donald G. Daus
Assistant Examiner—William A. Teoli, Jr.
Attorney, Agent, or Firm—Linda E. Hall; Janice E. Williams; Alan D. Lourie

[57] ABSTRACT

Process for preparing N-cyano-N'-methyl-1-aziridinoamidine by reacting aziridine with a N-cyano-N'-methyl-O-arylisourea.

2 Claims, No Drawings

PROCESS FOR PREPARING AN AZIRIDINE DERIVATIVE

This invention relates to the preparation of an aziridine derivative useful as an intermediate in the manufacture of the histamine-receptor antagonist drug cimetidine.

The preparation of N-cyano-N'-methyl-1-aziridinoamidine[2-cyano-1,1-ethylene-3-methylguanidine] and its conversion to cimetidine by reaction with 5-methyl-4-methylmercaptoimidazole[(4-methyl-1H-imidazol-5-yl)methanethiol] has been described by Toso et al, *Gazz. Chim. Ital.*, 1979, 109, 345–50. In the process described in this publication, the starting aziridine derivative is obtained by the reaction of aziridine with N-cyano-N',S-dimethylisothiourea;

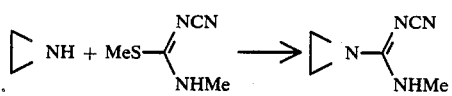

The reaction is carried out in acetonitrile in the presence of silver and hydroxyl ions, the silver being provided by silver nitrate, and results in the precipitation of silver mercaptide as by-product. Although the reaction is said to give a 64% yield of the aziridine derivative, m.p. 129°–30° C., experience has shown that when the reaction is carried out as described it is difficult to isolate the product from the reaction mixture in pure crystalline form, even in poor yield; moreover the process is economically unattractive, for the use of silver nitrate adds greatly to the cost of preparing cimetidine by this route, whose economics depend on the recovery of the silver and its recycling. The present invention is concerned with the problem of synthesising the aziridine derivative more economically.

One of several processes described for making cimetidine in British Pat. No. 1,397,436 involves reaction of a primary amine containing a substituent having an imidazole ring with an isourea or isothiourea;

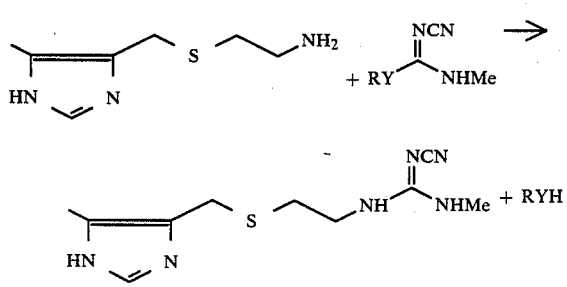

In the isourea or isothiourea Y is sulphur or oxygen (preferably sulphur) and R is lower alkyl (preferably methyl), aryl or arylalkyl. Where RY is methylthio, the reagent is the same as that used in the above Toso process, but the reaction using aziridine is markedly different because, unlike the corresponding reaction of British Pat. No. 1,397,436, it requires the presence of silver ions, without which no reaction takes place.

It has now been discovered that if instead of using N-cyano-N',S-dimethylsiothiourea, an N-cyano-N'-methyl-O-arylisourea is employed to react with aziridine, not only is the use of silver ions avoided, but the reaction is very fast and provides high yields of the aziridine derivative, and the product can be obtained by direct crystallisation from the reaction mixture.

The present invention therefore provides a process for the preparation of N-cyano-N'-methyl-1-aziridinoamidine, in which aziridine is reacted with a substituted amidine of the structure

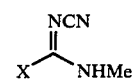

where X is a leaving group, characterised in that X is an aryloxy group.

Such substituted amidines are O-arylisoureas. Suitable aryloxy groups Ar are phenoxy, o-, m- and p-cresoxy, toloxy, chlorophenoxy, trifluoromethylphenoxy and nitrophenoxy groups: but for simplicity the aryloxy group is preferably a phenoxy group. Although a solvent, for instance acetonitrile, can be used if desired, preferably the reaction is carried out in the absence of any solvent other than aziridine itself. For this there is used aziridine in stoichiometric excess of that required for the reaction. Reaction can be conducted at from −20° to 40° C., preferably from 0° to 20° C.

A phenol is formed as by-product during the reaction, and recovery of the product uncontaminated by phenol may require chromatographic separation, for instance on silica gel using acetonitrile as eluant. It has been found that if in the amidine X is a phenoxy group and excess aziridine is used as the sole solvent, crystalline product is precipitated in the reaction mixture in high purity and yield and can be separated by a filtration which leaves nearly all the by-product phenol in the filtrate.

The product can be used to make cimetidine by reaction with 5-methyl-4-methylmercaptoimidazole as described in the existing literature.

An O-arylisourea used as starting material can be obtained as follows.

Preparation of N-cyano-N'-methyl-O-phenylisourea

A solution of methylamine in ethanol (33%, 0.939 g, containing 0.31 g, 0.010 mol methylamine) was diluted with isopropyl alcohol (3 ml) and added rapidly during 30 sec to a stirred suspension at 20° of diphenyl-N-cyanoimidocarbonate (2.38 g, 0.010 mol) in isopropyl alcohol (8 ml).

In 2–3 min. a clear solution was formed, and after heat was evolved a copious solid precipitate of N-methyl-N'-cyano-O-phenylisourea was formed. After 10 min this was filtered off and washed with cold isopropyl alcohol (2 ml), to give the product (1.25 g, 71.5%), m.p. 132.5°–133°, $R_f$ 0.82 (silica, acetonitrile).

Isourea starting materials having other aryl groups can be obtained by analogous methods, starting with the preparation of the diaryl-N-cyanoimidocarbonate from the corresponding dichlorodiaryloxymethane and cyanamide.

The invention is illustrated by the following Examples, in which, as in the above preparation, temperatures are in °C.

EXAMPLE 1

N-Cyano-N'-methyl-O-phenylisourea (0.471 g, 2.69 mmol) was added during 2 minutes to aziridine (0.521 g, 12.1 mmol) at 20° with stirring. Immediate solution occurred, some heat was evolved, and after 5 min a solid precipitate was formed. After 90 min excess aziridine was removed in an air stream at 20°, leaving an oily solid residue. This was dissolved in acetonitrile (10 ml) and the solution was absorbed on to silica gel (1.0 g), and remaining volatiles were removed by evaporation under reduced pressure at 20°. The solid obtained was added to the top of a column of silica gel (19.7 g, length 15 cm, diameter 2 cm) and the column eluted with acetonitrile. The elution of phenol was followed by TLC and after it was complete, subsequent eluate was collected and gave on evaporation to dryness under reduced pressure N-cyano-N'-methyl-1-aziridinoamidine (0.257 g, 77%), m.p. 130°–132.5°, $R_f$ 0.64–0.66 (silica, acetonitrile).

EXAMPLE 2

N-Cyano-N'-methyl-O-phenylisourea (10.0 g, 0.0571 mol) was added in half-gram batches during 6 min to aziridine (7.926 g, 0.184 mol) cooled to 0° and stirred. A solution was formed, from which after 5 min a colourless solid crystallised out. The reaction mixture was stirred at 20° for 90 min. and then cooled to 0° to complete crystallisation. Filtration and washing the residue with cold ether gave crystalline N-cyano-N'-methyl-1-aziridinoamidine (4.09 g, 57%), m.p. 134°–135°, $R_f$ 0.64–0.66 (silica, acetonitrile). Further product (1.78 g) was isolated from the ether washings, giving a total yield of 5.87 g, 82%.

What is claimed is:

1. A process for preparing N-cyano-N'-methyl-1-aziridino-amidine which comprises reacting an aziridine with a substituted amidine of the structure

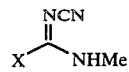

where X is an aryloxy group, in the absence of heavy metal salts and in which aziridine is employed as the sole solvent.

2. A process according to claim 1 in which X is phenoxy.

* * * * *